United States Patent
Veregin et al.

(10) Patent No.: US 11,579,138 B2
(45) Date of Patent: Feb. 14, 2023

(54) POLYMERIC ADDITIVES MADE USING BASE ADDITION AND RELATED METHODS

(71) Applicant: Xerox Corporation, Norwalk, CT (US)

(72) Inventors: Richard P. N. Veregin, Mississauga (CA); Kimberly D. Nosella, Ancaster (CA); Rosa M. Duque, Brampton (CA); Melanie Lynn Davis, Hamilton (CA); David R. Kurceba, Hamilton (CA); Cuong Vong, Hamilton (CA)

(73) Assignee: Xerox Corporation, Norwalk, CT (US)

( * ) Notice: Subject to any disclaimer, the term of this patent is extended or adjusted under 35 U.S.C. 154(b) by 549 days.

(21) Appl. No.: 16/701,312

(22) Filed: Dec. 3, 2019

(65) Prior Publication Data

US 2021/0164960 A1 Jun. 3, 2021

(51) Int. Cl.
| | |
|---|---|
| *G01N 33/44* | (2006.01) |
| *G01N 23/223* | (2006.01) |
| *H01J 49/10* | (2006.01) |
| *C08F 2/28* | (2006.01) |
| *C08F 220/18* | (2006.01) |
| *C08F 212/36* | (2006.01) |
| *C08F 220/34* | (2006.01) |

(52) U.S. Cl.
CPC .............. *G01N 33/442* (2013.01); *C08F 2/28* (2013.01); *C08F 212/36* (2013.01); *C08F 220/18* (2013.01); *C08F 220/34* (2013.01); *G01N 23/223* (2013.01); *H01J 49/105* (2013.01)

(58) Field of Classification Search
CPC ...... G01N 33/442; G01N 23/223; C08F 2/28; C08F 220/34; C08F 212/36; C08F 220/18; H01J 49/105
See application file for complete search history.

(56) References Cited

U.S. PATENT DOCUMENTS

| | | | |
|---|---|---|---|
| 8,663,886 B2 | 3/2014 | Vanbesien et al. | |
| 2015/0010862 A1 | 1/2015 | Matsumoto | |
| 2018/0181013 A1* | 6/2018 | Chiba | ................ G03G 9/0904 |
| 2020/0306830 A1 | 10/2020 | Veregin et al. | |
| 2020/0307027 A1 | 10/2020 | Veregin et al. | |
| 2020/0308328 A1 | 10/2020 | Veregin et al. | |
| 2020/0308330 A1 | 10/2020 | Veregin et al. | |

OTHER PUBLICATIONS

Extended Search Report issued on EP Application 20208771.4, dated Sep. 7, 2021.

* cited by examiner

*Primary Examiner* — Robert D Harlan
(74) *Attorney, Agent, or Firm* — Bell & Manning, LLC

(57) ABSTRACT

A method for assessing polymeric additive content A in a polymeric particle mixture may comprise determining a concentration B of a metal cation in a polymeric particle mixture comprising parent polymeric particles and polymeric additive particles, wherein the metal cation is selected from alkali earth metals and alkali metals, other than sodium (Na), and the metal cation is capable of forming a water-soluble base; determining a concentration C of the metal cation in the parent polymeric particles; determining a concentration D of the metal cation in the polymeric additive particles; and calculating a polymeric additive content A using formula $A=(B-C)/D$.

20 Claims, No Drawings

POLYMERIC ADDITIVES MADE USING BASE ADDITION AND RELATED METHODS

BACKGROUND

Polymeric additives have been used to supplement or replace silica and titania surface additives commonly used to enhance the properties of toner particles. Such polymeric additives are also used as flow aids for three-dimensional (3D) printing particles used in additive manufacturing applications such as selective laser sintering (SLS). However, because the polymeric additives are themselves organic in nature (as are the underlying toner and 3D printing particles), it has been challenging to accurately determine the quantity of polymeric additives present in a mixture of the polymeric additives with the toner/printing particles.

SUMMARY

Provided are methods for assessing polymeric additive content in a polymeric particle mixture of parent polymeric particles and polymeric additive particles. Also provided are methods for making polymeric additive compositions and methods for making the polymeric particle mixtures from those compositions.

In one aspect, methods for assessing polymeric additive content are provided. In embodiments, a method for assessing polymeric additive content A in a polymeric particle mixture comprises determining a concentration B of a metal cation in a polymeric particle mixture comprising parent polymeric particles and polymeric additive particles, wherein the metal cation is selected from alkali earth metals and alkali metals, other than sodium (Na), and the metal cation is capable of forming a water-soluble base; determining a concentration C of the metal cation in the parent polymeric particles; determining a concentration D of the metal cation in the polymeric additive particles; and calculating a polymeric additive content A using formula A=(B−C)/D.

In another aspect, methods of forming a polymeric additive composition for parent polymeric particles are provided. In embodiments, such a method comprises forming a polymeric additive latex via emulsion polymerization of monomers; and heating the polymeric additive latex for a time in the presence of an amount of a water-soluble base comprising a metal cation to form a processed polymeric additive latex, wherein the metal cation is selected from alkali earth metals and alkali metals, other than sodium (Na).

In another aspect, polymeric additive compositions for parent polymeric particles are provided. In embodiments, such a composition comprises a polymer formed from monomers comprising a monomer having a carbon to oxygen ratio in a range of 3 to 8; optionally, a monomer comprising two or more vinyl groups; optionally, an amine functional monomer; and a metal cation at a concentration in a range of from 400 ppm to 800 ppm, wherein the metal cation is selected from alkali earth metals and alkali metals, other than sodium (Na).

DETAILED DESCRIPTION

Provided are methods for assessing polymeric additive content in a polymeric particle mixture of parent polymeric particles and polymeric additive particles. Also provided are methods for making polymeric additive compositions and methods for making the polymeric particle mixtures from those compositions.

In one aspect, methods for assessing polymeric additive content in a polymeric particle mixture is provided. The methods comprise determining a concentration of a metal cation in a polymeric particle mixture comprising parent polymeric particles and polymeric additive particles. The polymeric particle mixture is a mixture of at least two different types of polymeric particles, i.e., the parent polymeric particles and the polymeric additive particles. By "different," it is meant that the compositions of the polymeric particles are different, but their size may also be different. The term "parent" is used since such particles are treated with the polymeric additive particles to modify certain properties of the parent polymeric particles, e.g., to enhance charge stability, enhance flow, enhance stability to environmental conditions, etc. The composition and size of each type of polymeric particle in the mixture depends upon the desired application. By way of illustration, for electrophotographic printing applications, the polymeric particle mixture may comprise toner parent polymeric particles and polymeric additive particles (which may be relatively smaller) absorbed and distributed on an outer surface of the parent toner particles. Polymeric particle mixtures used in some additive manufacturing applications such as SLS (Selective Laser Sintering) make use of similar configurations, although the composition/size of each type of polymeric particle differs from that of electrophotographic printing applications. For these and similar polymeric particle mixtures, it is desirable to be able to assess the content of the polymeric additive in the mixture in order to provide a measure of the quality of the polymeric particle mixture. However, an accurate assessment is challenging because both the parent polymeric particles and the polymeric additive particles are composed of organic materials and thus, may have similar elemental compositions.

The present disclosure addresses this challenge and provides efficient methods for accurately determining the quantity of polymeric additive particles in a mixture with parent polymeric particles and using the determination to ensure the mixture meets or exceeds an established quality control standard. The methods are further described below with reference to toner polymeric particle mixtures and 3D printing polymeric particle mixtures. However, the methods are generally applicable to a wide variety of polymeric particle mixtures.

The present methods are based on the addition of certain water-soluble bases during the processing of a polymeric additive latex which provides the polymeric additive particles. The water-soluble base comprises a metal cation selected from alkali metals (other than sodium (Na)) and alkali earth metals. By "water-soluble," it is meant that the base has solubility in water at room temperature (20-25° C.) of at least 20 g/L. In embodiments, the metal cation is selected from Li, K, Cs, Sr, and Ba. The corresponding anion in the water-soluble base is generally hydroxide (OH). In embodiments, the water-soluble base is selected from LiOH, KOH, CsOH, $Sr(OH)_2$, and $Ba(OH)_2$. Processing of the polymeric additive latex using these water-soluble bases is further described below.

As noted above, the present methods are further based on determining the concentration of the metal cation (derived from the water-soluble base) in the polymeric particle mixture comprising the parent polymeric particles and the polymeric additive particles. Various techniques may be used to determine the concentration of the metal ion, but illustrative suitable techniques include inductively coupled plasma (ICP) and X-ray fluorescence spectroscopy (XRF). Commercially available ICP and XRF instruments may be used.

In embodiments, the methods may comprise comparing the determined metal cation concentration to an expected metal cation concentration. As illustrated in the Example, below, the expected metal cation concentration may be calculated based on an amount of a polymeric additive composition that was mixed with a parent polymeric particle composition in forming the polymeric particle mixture and an amount of the water-soluble base that was added to a polymeric additive latex which provided the polymeric additive particles. Together, these two amounts translate into the amount of the metal cation that should be present in the polymeric particle mixture (i.e., the expected metal cation concentration) assuming ideal manufacturing conditions throughout the various steps of the processes of making the polymeric additive composition and the polymeric particle mixture. In embodiments, the expected metal cation concentration in the polymeric particle mixture is in a range of from 1 ppm to 50 ppm, which includes a range of from 1 ppm to 40 ppm and from 1 ppm to 30 ppm. In embodiments, it may be useful to also determine a baseline metal cation concentration of the metal cation in the parent polymeric particle composition itself. This baseline metal cation concentration can be subtracted from the metal cation concentration determined from the polymeric particle mixture in order to eliminate any contribution from the parent polymeric particles.

In embodiments, a method for assessing polymeric additive content A in a polymeric particle mixture is provided. The method comprises determining a concentration B of a metal cation in a polymeric particle mixture comprising parent polymeric particles and polymeric additive particles, wherein the metal cation is selected from alkali earth metals and alkali metals, other than sodium (Na), and the metal cation is capable of forming a water-soluble base; determining a concentration C of the metal cation in the parent polymeric particles; and determining a concentration D of the metal cation in the polymeric additive particles; and calculating polymeric additive content A using the formula: A=(B−C)/D. The concentration determinations may be carried out using the techniques described above, e.g., ICP or XRF. The value of A may be a value in pph (or weight %) or in any other units as long as the units are consistent for A, B, C and D.

Comparisons may be made between determined and expected metal cation concentration values or between calculated polymeric additive content A and target polymeric additive content A values as part of a quality control protocol. (The target polymeric additive content A value can refer to an amount of the polymeric additive particles actually added to the parent polymeric particles in forming the polymeric particle mixture.) Regarding the comparison between calculated and target polymeric additive content A values, the comparison can involve calculating the difference between the two values and comparing the difference to a threshold value. The threshold value could be zero, but it could also be some small value or range of ±0.02 pph to ±0.5 pph. This includes ±0.03 pph, ±0.04 pph, ±0.05 pph, etc. The result of the comparison may be an indication that the polymeric particle mixture passes the quality control standard (e.g., difference between the two values is ≤threshold value) or that the polymeric particle mixture fails the quality control standard (e.g., difference between the two values is >threshold value).

The steps of the present methods may be controlled by a system comprising a processor and a non-transitory computer-readable medium operably coupled to the processor, the computer-readable medium comprising instructions that, when executed by the processor, cause the system to perform one or more operations such as: initiating determinations of the metal cation concentration from the polymeric particle mixture, the parent polymeric particles, and/or the polymeric additive particles; calculating the expected metal cation concentration based on inputted data of the amount of the polymeric additive composition and the amount of the water-soluble base added during the processing of a polymeric additive latex; calculating polymeric additive content A using the formula described above; calculating differences between two values; comparing the differences to threshold values; and outputting an indication of passing or failing quality control.

Also provided are methods of making polymeric additive compositions and the polymeric particle mixtures. Briefly, the method of making the polymeric additive composition may comprise heating a polymeric additive latex for a time in the presence of an amount of the water-soluble base comprising the metal cation, thereby forming a processed polymeric additive latex. The method may further comprise recovering the polymeric additive particles from the processed polymeric additive latex. The method may further comprise making the polymeric additive latex via emulsion polymerization of monomers. The method of making the polymeric particle mixtures may comprise mixing a parent polymeric particle composition with a polymeric additive composition to form the polymeric particle mixture. The term "mixing" is not meant to be limiting, but can refer to the various techniques (some described below) used to combine and associate polymeric additive particles with parent polymeric particles. These methods, as well as the polymeric additive compositions and parent polymeric particle compositions, are further described below.

The phases "polymeric additive composition" and "parent polymeric particle composition" are meant to connote compositions comprising the respective particles, as opposed to the particular form of those compositions. The compositions may be in the form of a latex, recovered particles from the latex (which may be referred to as a dried latex), or an aqueous dispersion made from the recovered particles. By way of illustration, when the polymeric additive composition is in the form of a latex, the phrase "polymeric additive latex" may be used to describe the composition.

Polymeric Additive Compositions

The polymer of the polymeric additive compositions is formed from the polymerization of certain monomers. While not limited, in embodiments at least one monomer used in the polymerization is a monomer with a high carbon to oxygen (C/O) ratio, e.g., in a range of 3 to 8. The monomer having a high C/O ratio may be an aliphatic cycloacrylate such as cyclohexyl methacrylate. Other monomers may be included in the polymerization to form a copolymer. In embodiments, a monomer possessing two or more vinyl groups such as divinyl benzene is included. In embodiments, a monomer having an amine functionality such as dimethylaminoethyl methacrylate is included. Both the vinyl monomer and the amine functional monomer may be used with the monomer having the high C/O ratio.

Various amounts of the monomers may be used when forming the polymer of the polymeric additive compositions. The monomer having the high C/O ratio may be present at an amount in a range of from 60% to 99.4% by weight as compared to the weight of the copolymer. When present, the monomer possessing vinyl groups is present at an amount in a range of from 8% to 40% by weight as compared to the weight of the copolymer. When present, the amine functional monomer is present at an amount in a range of from 0.5% to 1.5% by weight as compared to the weight of the copolymer.

Emulsion polymerization may be used to form the polymer of the polymeric additive composition. In such a process, reactants may be added to a suitable reactor, such as a mixing vessel. Reactants may be dissolved in a solvent and an initiator may be added along with at least one surfactant. The reaction mixture may be mixed for various times (e.g., from 1 minute to 72 hours) at various temperatures (e.g., from 10-100° C.). Selection of the monomers, solvent, initiator, surfactants, the relative amount of these reactants, and the reaction conditions may be adjusted to generate polymers of various molecular weights and properties, depending upon the desired application. Illustrative component species, relative amounts, and reaction conditions are provided in the Example, below. However, the present disclosure is not particularly limited to the type of polymer formed. Others may be used as described in U.S. Pat. No. 8,663,886, U.S. patent application Ser. No. 16/369,013, filed Mar. 29, 2019, U.S. patent application Ser. No. 16/369,278, filed Mar. 29, 2019, U.S. patent application Ser. No. 16/369, 359, filed Mar. 29, 2019, and U.S. patent application Ser. No. 16/369,449, filed Mar. 29, 2019, each of which is hereby incorporated by reference in its entirety.

The composition resulting from the emulsion polymerization is a polymeric additive latex comprising the polymer thus formed. Prior to using the polymeric additive latex, it is heated for a time in the presence of an amount of any of the water-soluble bases described above. The application of heat may follow a heating protocol involving various combinations of maintaining certain temperatures for certain period of times and heating to other temperatures at certain heating rates. However, these temperatures may be in a range of from 60° C. to 95° C. and the total heating time may be in a range of from 30 minutes to 3 hours. The amount of the water-soluble base depends upon the desired pH, which in turn depends upon the composition of the polymeric additive latex. The pH may be in a range of from 4 to 9. Illustrative heating protocols, amount of water-soluble base, and pH are provided in the Example, below.

The polymeric additive latex, thus processed via base addition, may then be used to form the polymeric particle mixtures. In embodiments, the polymeric additive particles are recovered from the processed polymeric additive latex, e.g., by filtration, drying, centrifugation, spray drying, freeze drying, etc., and subsequently mixing with the desired parent polymeric particles. However, the processed polymeric additive latex itself may be used in forming the polymeric particle mixtures. By way of illustration, parent polymeric particles may be dipped into the processed polymeric additive latex, the processed polymeric additive latex may be sprayed onto the parent polymeric particles, etc. Another option involves dispersing recovered polymeric additive particles into water to form an aqueous dispersion and using the aqueous dispersion in forming the polymeric particle mixtures as described with respect to the processed polymeric additive latex. These options mean that the "polymeric additive compositions" described above can refer to the processed polymeric additive latex, the recovered polymeric additive particles, or the aqueous dispersion of recovered polymeric additive particles. In embodiments, the polymeric additive composition is recovered polymeric additive particles, which may simply be referred to as the polymeric additive particles.

Similarly, in forming the polymeric particle mixtures, the parent polymeric particles may be used in various forms, e.g., as a latex, recovered particles (i.e., dried latex), or an aqueous dispersion of recovered particles. As noted above, these forms are encompassed by the phrase "parent polymeric particle composition."

The size of the polymeric additive particles depends upon their composition and processing conditions. However, the polymeric additive particles may have an average or median particle size (d50) of from 70 nm to 250 nm.

Regardless of how the polymeric particle mixtures are formed, the amount of the polymeric additive particles in the mixture is selected to modify certain properties of the parent polymeric particles as noted above. In embodiments, the polymeric additive particles are present in an amount of from 0.1% to 5% by weight of the parent polymeric particles, from 0.2% to 2% by weight of the parent polymeric particles, or from 0.5% to 2% by weight of the parent polymeric particles. Thus, these values may be referred to as the target polymeric additive content A values described above.

Parent Polymeric Particle Compositions

Polymeric additive particles may be mixed with a variety of types of parent polymeric particles to form the polymeric particle mixtures. Illustrative parent polymeric particles include toner parent polymeric particles and 3D printing parent polymeric particles. Regarding toner parent polymeric particles, the type of toner parent polymeric particles (e.g., its composition, properties, method of formation, etc.) is not particularly limited. However, in embodiments, the toner parent polymeric particles are core-shell particles comprising both crystalline and amorphous polyesters. Various colorants and waxes may be included in such parent toner particles. Such toner parent polymeric particles may be formed via emulsion-aggregation of polymeric latexes, optionally with one or more pigment dispersions and optionally with one or more wax dispersions. The toner parent polymeric particles may have an average or median (d50) of from 4 μm to 10 μm. Other toner parent polymeric particles may be used, including those described in U.S. Pat. No. 8,663,886 and U.S. patent application Ser. No. 16/369,013, filed Mar. 29, 2019, each of which is hereby incorporated by reference in its entirety.

Regarding 3D printing parent polymeric particles, again, the type of 3D printing parent polymeric particles is not particularly limited. In embodiments, the polymer of the 3D printing parent polymeric particles may be a polyamide (e.g., PA6, PA12), a thermoplastic polyurethane, a polyimide, a polyesterimide, high density polyethylene, polylactic acid, a polyalkenoate such as polyhydroxybutyrate or polyhydroxyvalerate, or polyether ether ketone. Other 3D printing parent polymeric particles may be used, including those described in U.S. patent application Ser. No. 16/369,278, filed Mar. 29, 2019, U.S. patent application Ser. No. 16/369, 359, filed Mar. 29, 2019, and U.S. patent application Ser. No. 16/369,449, filed Mar. 29, 2019, each of which is hereby incorporated by reference in its entirety.

Polymeric Particle Mixtures and Applications

As noted above, various techniques may be used to combine and associate the polymeric additive particles with the parent polymeric particles to form the polymeric particle mixtures. Illustrative amounts of the polymeric additive particles in the polymeric particle mixtures have been provided above. In addition to the polymeric additive particles, other additives may be used with the parent polymeric particles, e.g., silica surface additives, titania surface additives, or both. Illustrative amounts and other types of additives that may be used include those described in U.S. Pat. No. 8,663,886, U.S. patent application Ser. No. 16/369,013, filed Mar. 29, 2019, U.S. patent application Ser. No. 16/369,278, filed Mar. 29, 2019, U.S. patent application Ser. No. 16/369,359, filed Mar. 29, 2019, and U.S. patent application Ser. No. 16/369,449, filed Mar. 29, 2019, each of which is hereby incorporated by reference in its entirety.

Depending upon the application, the polymeric particle mixture may be combined with other components, e.g., a carrier to form a developer for electrophotographic printing, a filler to aid formation of a 3D article in additive manufacturing such as SLS, etc. Again, these applications and such components have been described in in U.S. Pat. No. 8,663,886, U.S. patent application Ser. No. 16/369,013, filed Mar. 29, 2019, U.S. patent application Ser. No. 16/369,278, filed Mar. 29, 2019, U.S. patent application Ser. No. 16/369,359, filed Mar. 29, 2019, and U.S. patent application Ser. No. 16/369,449, filed Mar. 29, 2019, each of which is hereby incorporated by reference in its entirety.

Regardless of the final application for the polymeric particle mixtures, as described above, the present methods may be used to accurately and efficiently determine the content of the polymeric additive particles in the mixtures to ensure these mixtures meet established quality control standards and will be optimal for their intended use.

The present disclosure also encompasses the polymeric additive compositions and the polymeric particle mixtures described above. These materials may be characterized by their metal cation concentration. Regarding the polymeric additive compositions, the metal cation concentration may be in a range of from 400 ppm to 2000 ppm. This includes a range of from 400 ppm to 1000 ppm, from 400 ppm to 800 ppm, and from 400 ppm to 600 ppm. Regarding the polymeric particle mixtures, the metal cation concentration will be greater than that of a baseline metal cation concentration in the parent polymeric particles and may be greater by an amount in a range of from 1 ppm to 50 ppm. This includes a range of from 1 ppm to 40 ppm and from 1 ppm to 30 ppm. The metal cation may be any of those described above with respect to the water-soluble bases.

Example

Polymeric Additive Compositions

A first polymeric additive latex (Polymeric Additive Latex A) was prepared at a 5-gal scale and a second polymeric additive latex (Polymeric Additive Latex B) was prepared at a 300-gal scale. Both latexes were prepared via emulsion polymerization using a mixture of monomers including 74.2 weight % cyclohexyl methacrylate (CHMA), 25 weight % divinyl benzene (DVB), and 0.8 weight % dimethylaminoethyl methacrylate (DMAEMA) at 20 weight % solids, and 14 weight % sodium laureth sulfate (SLS) used upfront in the reactor. Both latexes were reacted at 77° C. using ammonium persulfate (APS) as the initiator to begin the reaction. The reaction continued for 2 hours at 77° C. After the reaction, both latexes were heated according to the following protocol: 1 hr at 77° C., 2 hrs ramp up to 87° C., and 2 hrs at 87° C. During the heating, 0.941 kg of 0.4% KOH solution was added to the first latex while 22 kg of 0.4% NaOH solution was added to the second latex. Then both latexes were cooled to room temperature. The details for each latex are shown in Tables 1A and 1B, below.

Regardless of the final application for the polymeric particle mixtures, as described above, the present methods may be used to accurately and efficiently determine the content of the polymeric additive particles in the mixtures to ensure these mixtures meet established quality control standards and will be optimal for their intended use.

TABLE 1A

Latex Details.

| | Formulation | | | |
|---|---|---|---|---|
| Example | % Solids | DMAEMA | % SLS reactor | % APS |
| Polymeric Additive Latex B | 20 | 0.8% | 14 | 3.42 |
| Polymeric Additive Latex A | 20 | 0.8% | 14 | 8.39 |

TABLE 1B

Latex Details.

| | Reaction Conditions | | Latex Properties | | | | |
|---|---|---|---|---|---|---|---|
| | | | | Gas Chromatography | | | |
| Example | Mixing rpm | Latex Processing | PS (nm) | CHMA (ppm) | DMAEMA (ppm) | DVB (ppm) | Total (ppm) |
| Polymeric Additive Latex B | 59/66 | 1 hr 77° C. + 2 hr ramp to 87° C. + 2 hr 87° C. | 99 | 288 | ND | 19 | 307 |
| Polymeric Additive Latex A | 59/66 | 1 hr 77° C. + 2 hr ramp to 87° C. + 2 hr 87° C. | 106 | 166 | ND | 54 | 201 |

Mixture with Toner Parent Polymeric Particles

XEROX® 700 Digital Color Press black toner parent polymeric particles were mixed in a 10-L Henschel using standard conditions with surface additives as follows. One blend added 0.95 pph of recovered polymeric additive particles from Polymeric Additive Latex A (i.e., spray-dried Polymeric Additive Latex A) a second blend added 0.95 pph of recovered polymeric additive particles from Polymeric Additive Latex B (i.e., spray-dried Polymeric Additive Latex B), and a third blend was a control using 1.4 pph of a sol-gel silica instead of the recovered polymeric additive particles To all blends were also added following additive composition by weight of the toner particles: 2.3 pph 40 nanometer silica, 0.88 pph 40 nanometer titania, 0.14 strontium titanate and 0.09 pph zinc stearate.

Bench Developer Evaluation

For each additive blended toner prepared as described above, 1.5 grams of the blended toner and 30 grams of Xerox® 700 carrier in a 60 mL glass bottle were combined. Samples were conditioned three days in a low-humidity zone (J zone) at 21.1° C. and 10% RH, and in a separate sample in a high humidity zone (A zone) at about 28° C./85% relative humidity. The developers with additive blended toner were charged in a Turbula® mixer for 60 minutes. The triboelectric charge of the toner was measured using a charge spectrograph using a 100 V/cm field. The toner charge (Q/D) was measured visually as the midpoint of the toner charge distribution. The charge was reported in millimeters of displacement from the zero line. (The displacement in mm can be converted to Q/D charge in femtocoulombs per micron by multiplication by 0.092 femtocoulombs/mm.)

The blended toner charge per mass ratio (Q/M) was also determined by the total blow-off charge method, measuring the charge on a faraday cage containing the developer after removing the toner by blow-off in a stream of air. The total charge collected in the cage is divided by the mass of toner removed by the blow-off, by weighing the cage before and after blow-off to give the Q/M ratio.

Toner blocking was determined by measuring the toner cohesion at elevated temperature above room temperature for the toner blended with surface additives. Toner blocking measurement was completed as follows: two grams of additive blended toner was weighed into an open dish and conditioned in an environmental chamber at the specified elevated temperature and 50% relative humidity. After about 17 hours, the samples were removed and acclimated in ambient conditions for about 30 minutes. Each re-acclimated sample was measured by sieving through a stack of two pre-weighed mesh sieves, which were stacked as follows: 1000 μm on top and 106 μm on bottom. The sieves were vibrated for about 90 seconds at about 1 mm amplitude with a Hosokawa flow tester. After the vibration was completed, the sieves were re-weighed and toner blocking was calculated from the total amount of toner remaining on both sieves as a percentage of the starting weight. Thus, for a 2-gram toner sample, if A is the weight of toner left the top 1000 μm screen and B is the weight of toner left the bottom 106 μm screen, the toner blocking percentage is calculated by: % blocking=50 (A+B).

As shown in Table 2, nearly equivalent charge was obtained for the KOH and NaOH processed polymeric additive latexes, very similar to the control. Blocking was slightly worse for the KOH and NaOH processed polymeric additive latexes as compared to the control, but all are within a small range of each other, ±1° C. The data in Table 2 shows that use of a metal ion other than Na does not substantially change the performance of the polymeric additive in the toner example shown herein.

TABLE 2

Results of Bench Developer Evaluation

| | Az Q/d | Az Q/m | Jz Q/d | Jz Q/m | Blocking Onset |
|---|---|---|---|---|---|
| Control Polymeric Particle Mixture | 5.5 | 27 | 10.9 | 56 | 53.3 |
| Polymeric Particle Mixture B 0.95% Dried Polymeric Additive Latex B (NaOH latex treatment) | 6.1 | 31 | 11.0 | 57 | 52.2 |

TABLE 2-continued

Results of Bench Developer Evaluation

| | Az Q/d | Az Q/m | Jz Q/d | Jz Q/m | Blocking Onset |
|---|---|---|---|---|---|
| Polymeric Particle Mixture A 0.95% Dried Polymeric Additive Latex A (KOH latex treatment) | 6.2 | 31 | 11.4 | 57 | 51.2 |

Detection of Metal Cation ($K^+$)

A commercial ICP instrument (ICAP 6000 series Inductively Coupled Plasma-Optical Emission Spectrometer (ICP-OES) by Thermo Electron Corporation) was used to determine the concentration of potassium metal ions in the following samples: Dried Polymeric Additive Latex A (tested in triplicate), Polymeric Particle Mixture A, and the Toner Parent Polymeric Toner Particles. The results are shown in Table 3, below.

TABLE 3

Results from ICP Analysis.

| Sample ID | Test | Result | Units |
|---|---|---|---|
| Polymeric Particle Mixture A | ICP-K | 30.61 | ppm |
| Toner Parent Polymeric Toner Particles | ICP-K | 25.84 | ppm |
| Dried Polymeric Additive Latex A (test 1) | ICP-K | 636.65 | ppm |
| (test 2) | ICP-K | 604.15 | ppm |
| (test 3) | ICP-K | 617.25 | ppm |

It was calculated that the Dried Polymeric Additive Latex A should contain 619 ppm $K^+$ since 0.941 kg of a 0.4% KOH solution was added to 18 kg of the Polymeric Additive Latex A (20 weight % solids) and KOH assay at 85%. Table 3 shows that the actual measured value using ICP averaged over three measurements was also 619 ppm. This value of 619 ppm is D in the formula A=(B−C)/D. As noted above, Polymeric Particle Mixture A contains 0.95 weight % of these recovered polymeric additive particles. This means the concentration of $K^+$ should be 619×0.95/100=5.88 ppm (expected metal cation concentration). Subtracting the $K^+$ concentration of the Toner Parent Polymeric Toner Particles (C in the formula above) from that of the Polymeric Particle Mixture A (B in the formula) results in a $K^+$ concentration of (30.61−25.84)=4.8 ppm (determined metal cation concentration). The difference between the two values is about 1 ppm.

Using the values of B=30.61, C=25.84 and D=619 ppm, A can then be calculated as (30.61−25.84)/619)=0.0078 or 0.78 pph. This is a little lower than expected, since the blend input weighed was 0.95 pph. This may indicate that there was some additive actually lost in the blending process. However, the measurements were conducted prior to optimizing the analysis and assessing the exact measurement error limits. Therefore, in this case, there may be an offset due to the measurement error of the ICP instrument and the calibration of the instrument for K ion. It is well known that the measurement error may be reduced or eliminated by running a controlled Measurement System Analysis (MSA) on the ICP instrument. It is noted that ICP instruments are able to detect metallic ions to <1 ppm. Thus, the results establish that the disclosed measurement protocol may be used to assess polymeric additive content in a polymeric particle mixture. Accuracy may be increased using rigorous calibration of the metal ion of interest and optimization of the measurement system using known analytical techniques such as standard additions and MSAs, which also will establish the limits of measurement error for the measurement protocol The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

It will be appreciated that variants of the above-disclosed and other features and functions or alternatives thereof, may be combined into many other different systems or applications. Various presently unforeseen or unanticipated alternatives, modifications, variations or improvements therein may be subsequently made by those skilled in the art, which are also intended to be encompassed by the following claims.

What is claimed is:

1. A method for assessing polymeric additive content A in a polymeric particle mixture, the method comprising:
    determining a concentration B of a metal cation in a polymeric particle mixture, the polymeric particle mixture comprising parent polymeric particles and polymeric additive particles, wherein the metal cation is selected from alkaline earth metals and alkali metals, other than sodium (Na), and the metal cation is capable of forming a water-soluble base;
    determining a concentration C of the metal cation in the parent polymeric particles;
    determining a concentration D of the metal cation in the polymeric additive particles; and
    calculating a polymeric additive content, A, of the polymeric additive particles in the polymeric particle mixture using formula A=(B−C)/D.

2. The method of claim 1, wherein the polymeric particle mixture is a toner polymeric particle mixture and the parent polymeric particles are toner parent polymeric particles.

3. The method of claim 1, wherein the polymeric particle mixture is a 3D printing polymeric particle mixture and the parent polymeric particles are 3D printing polymeric particles.

4. The method of claim 1, wherein the metal cation is selected from Li, K, Cs, Sr, and Ba.

5. The method of claim 4, wherein the water-soluble base is selected from LiOH, KOH, CsOH, Sr(OH)$_2$, and Ba(OH)$_2$.

6. The method of claim 1, wherein determining the concentrations B, C, and D of the metal cation is carried out using inductively coupled plasma (ICP) or X-ray fluorescence spectroscopy (XRF).

7. The method of claim 1, wherein the concentration D of the metal cation in the polymeric additive particles is in a range of from 400 ppm to 2000 ppm.

8. The method of claim 1, wherein the polymeric additive particles were recovered from a polymeric additive latex treated with the water-soluble base.

9. The method of claim 1, further comprising calculating a difference between the calculated polymeric additive content A and a target polymeric additive content A and comparing the difference to a threshold value.

10. The method of claim 9, wherein the threshold value is ±0.05 pph.

11. The method of claim 1, wherein a difference between the concentration B of the metal cation in the polymeric particle mixture and the concentration C of the metal cation in the parent polymeric particles is in a range of from 1 ppm to 30 ppm.

12. The method of claim 1, further comprising heating a polymeric additive latex for a time in the presence of an amount of the water-soluble base comprising the metal cation to form a processed polymeric additive latex comprising the polymeric additive particles.

13. The method of claim 1, further comprising mixing the parent polymeric particles with the polymeric additive particles to form the polymeric particle mixture.

14. A method of forming a polymeric additive composition for parent polymeric particles, the method comprising:
    forming a polymeric additive latex via emulsion polymerization of monomers; and
    heating the polymeric additive latex for a time in the presence of an amount of a water-soluble base comprising a metal cation to form a processed polymeric additive latex comprising polymeric additive particles, wherein the metal cation is selected from alkaline earth metals and alkali metals, other than sodium (Na).

15. The method of claim 14, further comprising recovering the polymeric additive particles from the processed polymeric additive latex and mixing the recovered polymeric additive particles with parent polymeric particles to form a polymeric particle mixture.

16. The method of claim 14, wherein the monomers comprise cyclohexyl methacrylate, divinyl benzene, and dimethylaminoethyl methacrylate.

17. The method of claim 14, wherein the metal cation is selected from Li, K, Cs, Sr, and Ba.

18. The method of claim 14, wherein the water-soluble base is selected from LiOH, KOH, CsOH, Sr(OH)$_2$, and Ba(OH)$_2$.

19. The method of claim 15, further comprising:
    determining a concentration B of the metal cation in the polymeric particle mixture;
    determining a concentration C of the metal cation in the parent polymeric particles;
    determining a concentration D of the metal cation in the recovered polymeric additive particles; and
    calculating a polymeric additive content, A, of the recovered polymeric additive particles in the polymeric particle mixture in the polymeric particle mixture using formula A=(B−C)/D.

20. The method of claim 19, further comprising calculating a difference between the calculated polymeric additive content A and a target polymeric additive content A and comparing the difference to a threshold value.

* * * * *